United States Patent [19]
Bell

[11] Patent Number: 5,817,608
[45] Date of Patent: Oct. 6, 1998

[54] CLEANSING COMPOSITIONS CONTAINING CONDITIONING AGENTS AND REFINED AGRICULTURAL GRAINS

[75] Inventor: Stephen R. Bell, Harwinton, Conn.

[73] Assignee: Brimms Inc., Tonawanda, N.Y.

[21] Appl. No.: 697,527

[22] Filed: Aug. 26, 1996

[51] Int. Cl.$^6$ ................................ C11D 3/382; C11D 1/82
[52] U.S. Cl. ..................... 510/122; 510/121; 510/139; 510/462; 510/463; 510/466; 510/470
[58] Field of Search ...................... 510/121, 122, 510/462, 463, 466, 470, 139, 151

[56] References Cited

U.S. PATENT DOCUMENTS

| | | | |
|---|---|---|---|
| 3,933,672 | 1/1976 | Bartolotta et al. | 252/116 |
| 4,115,313 | 9/1978 | Lyon et al. | 252/309 |
| 4,211,901 | 7/1980 | Matsuda et al. | 200/83 B |
| 4,390,469 | 6/1983 | Oughton | 260/123.5 |
| 4,673,525 | 6/1987 | Small et al. | 252/132 |
| 4,728,457 | 3/1988 | Fieler et al. | 252/174.15 |
| 4,812,253 | 3/1989 | Small et al. | 252/132 |
| 5,023,080 | 6/1991 | Gupta | 424/405 |
| 5,055,300 | 10/1991 | Gupta | 424/409 |
| 5,076,953 | 12/1991 | Jordan et al. | 252/108 |
| 5,079,005 | 1/1992 | Gupta | 424/408 |
| 5,169,660 | 12/1992 | Collins et al. | 426/271 |
| 5,264,144 | 11/1993 | Moroney et al. | 252/117 |

FOREIGN PATENT DOCUMENTS

| | | |
|---|---|---|
| 2721210 | 6/1994 | France . |
| 2170216 | 7/1986 | United Kingdom . |

*Primary Examiner*—Mukund J. Shah
*Assistant Examiner*—Bruck Kifle
*Attorney, Agent, or Firm*—Phillips, Lytle, Hitchcock, Blaine & Huber

[57] ABSTRACT

A personal cleansing composition, suitable for use as a soap or a shampoo, contains at least one conditioning agent, such as silicone. The composition also contains a refined agricultural grain, such as oats, that has been at least partially defatted and that has at least some of its bran removed. The conditioning agent is carried by the grain, and is substantially insoluble in the wetted composition.

1 Claim, No Drawings

CLEANSING COMPOSITIONS CONTAINING CONDITIONING AGENTS AND REFINED AGRICULTURAL GRAINS

TECHNICAL FIELD

This invention relates generally to the field of personal cleansing compositions (e.g., soaps, shampoos, etc.) containing conditioning agents, and, more particularly, to improved cleansing compositions containing refined agricultural grain(s) (e.g., oats, etc.) for enhancement of processing, performance and mildness characteristics, and improved deposition of the conditioning agents.

BACKGROUND ART

Manufacturers of cleansing products and compositions have long recognized that cleansing products can leave the skin stripped of all oil, and therefore very dry. The reason for this is that the surfactants and soaps in such cleansing products cannot differentiate between facial dirt and naturally-occurring oils that our bodies produce to protect the skin. Thus, such cleansing products typically remove both dirt and protective oils, leaving the skin feeling dry and often irritated.

To prevent the skin from being overly dried, cleansing products have been formulated with various conditioners or refatting agents. These refatting agents are typically insoluble in water. Examples of such refatting agents include silicones (e.g., dimethicones and other water-insoluble silicones), mineral oil, various vegetable oils, lecithin, oat oil, and the like. The general intent is to deposit on the skin, a uniform and continuous layer of the conditioning agent(s) to replace that which was removed during washing. However, these refatting agents may be serious foam suppressants. Silicone is marketed as a foam suppressant to the food and cosmetic industries. Therefore, while it is possible to make a cleansing product with refatting agents that do not dry out the skin, these will not foam and lather as well as the same product made without the refatting agent. The reason for this is that the surfactants in the product solubilize the refatting agents, and such refatting agents then become a part of the surface chemistry of the foam. This alters the surface tension of bubbles, and causes the foaming to be reduced.

The use of water-insoluble conditioners, particularly silicone, in shampoos and cleansing bars is well known in the prior art. See, e.g., U.S. Pat. No. 4,728,457 and published British Patent Application No. GB 2 170 216 A, the aggregate disclosures of which are hereby incorporated by reference. While these references disclose silicone- containing compositions and formulations, they do not provide answers to all of the problems encountered in making a satisfactory product.

One persistent problem has been to develop effective processing methods for incorporating a dispersed, insoluble, non-volatile silicone material in the composition, whether in solid or liquid form. Conventional methods for making silicone-containing liquid cleansing products have heated a mixture of ingredients, with the silicone/conditioning agent being added either before or after the heating step. This process is energy-intensive, and may result in a less than stable product.

Another problem has been that of causing an effective, uniform deposition of conditioning agents onto the skin and/or hair. The very nature of cleansing products is to remove materials, such as silicone and petrolatum, from the skin and/or hair. Moreover, cleansed skin and hair is basically hydrophilic, and is not a preferred site for deposition of hydrophobic materials, such as silicone. Therefore, a complex set of conditions must exist during the act of washing with conditioner-containing cleansing compositions, for the conditioner to adequately deposit itself on the skin and hair. Two critical parameters in this deposition process are soap bubble viscosity and the droplet size of the silicone/conditioning agent in the lather. Even then, the deposition of conditioning agent(s) from conventional cleansing compositions may be less than optimum, when measured in terms of the amount and uniformity of silicone material deposited on to the skin and hair.

DISCLOSURE OF THE INVENTION

The present invention provides improved cleansing compositions that contain conditioning agents. The improved compositions also include refined agricultural grain(s) (e.g., oats, wheat, barley, etc.) for enhancement of processing, performance and mildness features.

The improved cleansing compositions have at least one conditioning agent. The improvement comprises adding to such compositions a refined agricultural grain, the grain being at least partially defatted and having at least some of its bran removed, such that the conditioning agent will be carried by the grain to keep the conditioning agent substantially insoluble in the wetted composition.

Accordingly, the general object of this invention is to provide an improved cleansing composition for use as a soap, shampoo or other personal cleanser.

Another object is to provide an improved cleansing composition containing a refatting or conditioning agent, which has a foamability comparable to a composition not having the refatting agent.

Another object is to provide an improved cleansing composition that affords the desirable capability of improved uniformity of deposition.

Still another object is to provide improved cleansing compositions having conditioning agents that leave the skin feeling moisturized.

These and other objects and advantages will become apparent from the foregoing and ongoing written specification, and the appended claims.

DESCRIPTION OF THE PERFERRED EMBODIMENTS

Applicant has surprisingly found that by using gum/bran-free grain flours, not only is significantly better deposition of silicone from conditioner-containing cleansing products achieved, but also the product performs better and is milder.

The use of specifically-processed agricultural grains is important because such grains can carry the refatting agents in insoluble form in such cleansing formulations. The grains are believed to absorb the refatting ingredients on to their surfaces, and the grain/oil mixtures remain suspended in the formulation. The result is a cleansing product that has a foaming power equal to a corresponding formula without the refatting agent. The formula with the grain/oil mixture leaves the skin feeling moisturized, whereas the regular formula dries out the skin.

The agricultural grains are refined by removal of the bran, and by subjecting them to a process which causes them to be at least partially defatted. Various processes for refining agricultural grains are known. These are representatively shown and described in U.S. Patents No. 5,023,080, 5,055, 300, 5,079,005, 4,211,901, 5,169,660 and 4,390,469, the aggregate disclosures of which are hereby incorporated by reference. Upon information and belief, others have supplied oat-derived materials to the personal care industry as natural emulsifiers. Such emulsifiers would render silicones soluble, and therefore render them ineffective for use as conditioning agents. Applicant has discovered that certain oat-derived materials can be used as carrying and/or suspending agents, rather than as emulsifiers. Moreover, it is further believed that others have counselled that a functional protein/silicone composition cannot be achieve by means of a simple mixture, as applicant has done here.

In general, prior art cleansing formulations have included the following generic types of elements: (1) a fragrance, (2) a surfactant, (3) one or more preservatives, (4) one or more suspending agents, (5) one or more coloring agents, and (6) one or more skin conditioning agents.

Using specially-processed agricultural grains in conditioner-containing personal cleansing compositions is believed to aid in the initial processing and manufacturing of the product, to aid in the post-formulation stability of the product, and is further believed to enhance product performance. With respect to the improvements in processing, silicones can be simply added to the liquid shampoos without heating the mixture. Upon information and belief, present processes require that the mixture be heated to an excess of 50° C. during processing. High-shear mixing equipment is not absolutely required. Moreover, because such agricultural grains can both suspend and thicken the product, they do the job of what now requires two or more raw materials. This is believed to improve the overall product stability. Finally, such agricultural grains improve the lathering and conditioning performance of the product. Oats improve foam stability, which means the lather is richer and creamier, and stays that way longer. This is demonstrated by foam height and foam density experiments, as discussed infra. Without the oats, silicone will act to suppress the foam. With oats, foaming is equivalent to the control product. Conditioning is also improved because oats, by orienting themselves along the air-surface portion of the soap bubble, are more likely to come in contact with the skin. The protein portion of oats has an affinity for the skin and/or hair surface. Because the oats are complexed with the silicone, the silicone is better deposited on the skin and hair.

Accordingly, the present invention broadly provides an improved cleansing composition that contains at least one conditioning agent, such as silicon, mineral oil, lecithin, oat oil or the like. The improved composition also contains a refined agricultural grain, typically oats, barley or wheat. The grain is at least partially defatted and has at least some of its bran removed. The conditioning agent will be carried by the grain to keep the conditioning agent insoluble in the wetted composition.

EXPERIMENTAL SUPPORT DATA

Rubine Dye Test

To show that oat flour is substantive (ie., deposits on hair), the Rubine Dye Test is utilized. This is a well-recognized and widely-accepted test in the industry. Rubine dye is an anionic material, and, in the presence of cationic materials, changes white wool to a pink-red color if the cationic material is present. This test is utilized for screening purposes, and is not intended to be used to determine quantitative deposition. Test results were positive for deposition from conditioner- containing 2-in-1 shampoo test solution.

Foam Stability Testing

Foam stability was measured using a Ross-Miles apparatus, which measures the foam height of surfactant solutions. Foam height of the improved formulation was compared to foam height of a standard cleansing formulation, as shown in the following table:

TABLE 1

Formulations Used In Foam Stability Tests

| Ingredient | Reference Formula | Improved Formula |
| --- | --- | --- |
| TEA - Lauryl Sulfate | 25.0 | 25.0 |
| Lauramide DEA | 5.0 | 5.0 |
| PEG 6000 Distearate | 1.5 | 1.5 |
| Citric Acid | Adjust to Ph 7.0 | Adjust to Ph 7.0 |
| Cellulosic-Based Gum | 0.2 | 0.2 |
| Oat Flour (Canamino CI-15) | — | 1.5 |
| F-10,000 (Siltech) (10,000 cst dimethicone) | — | 2.0 |
| Preservative | 0.1 | 0.1 |
| Water | bal. | bal. |

TABLE 2

Results of Foam Stability Tests

| | Foam Height (mm) | 30-Minute Foam Stability (% of Initial Height) |
| --- | --- | --- |
| Reference Formula (per Table 1) | 225 | 88.9 |
| Improved Formula (per Table 1) | 235 | 90.6 |

Wet/Dry Hair Combability Test

The combability of both virgin and bleached hair was determined using an Instron method developed by M. L. Garcia and J. Diaz, "Combability Measurements on Human Hair", *Journal of Society of Cosmetic Chemists*, 27:379–398 (1976). These measurements were done on both wet and dry hair. Using the formulations in Table 3, the combability results reported in Table 4 show that oat flour is far superior to any of the other test formulations. Hence, oat flour significantly aids in the deposition of silicone.

TABLE 3

Conditioning Shampoo Formulations

| Ingredient | 1 | 2 | 3 | 4 | 5 | 6 | 7 | 8 |
|---|---|---|---|---|---|---|---|---|
| Na Lauryl Sulfate | — | — | — | — | 7.5 | 7.5 | 7.5 | 7.5 |
| Na Lauryl Sulfate | — | — | — | — | 7.5 | 7.5 | 7.5 | 7.5 |
| TEA Lauryl Sulfate | 20.0 | 20.0 | 20.0 | 20.0 | — | — | — | — |
| Cocamide MEA | 3.0 | 3.0 | 3.0 | 3.0 | 3.0 | 3.0 | 3.0 | 3.0 |
| Hydromethylcellulose | 0.2 | 0.2 | 0.2 | 0.2 | 0.2 | 0.2 | 0.2 | 0.2 |
| NaCl | 1.0 | 1.0 | 1.0 | 1.0 | 1.0 | 1.0 | 1.0 | 1.0 |
| Citric Acid | 0.2 | 0.2 | 0.2 | 0.2 | 0.2 | 0.2 | 0.2 | 0.2 |
| Colloidal Oatmeal | — | — | 1.0 | — | — | — | 1.0 | — |
| Specially-Processed Oats | — | — | — | 1.0 | — | — | — | 1.0 |
| Dimethicone | — | 2.0 | 2.0 | 2.0 | — | 2.0 | 2.0 | 2.0 |
| PEG - Distearate | 1.0 | 1.0 | 1.0 | 1.0 | 1.0 | 1.0 | 1.0 | 1.0 |
| Cetyl Alcohol | 1.0 | 1.0 | 1.0 | 1.0 | 1.0 | 1.0 | 1.0 | 1.0 |
| Preservative | 0.1 | 0.1 | 0.1 | 0.1 | 0.1 | 0.1 | 0.1 | 0.1 |
| Fragrance | 0.5 | 0.5 | 0.5 | 0.5 | 0.5 | 0.5 | 0.5 | 0.5 |
| Water | bal. | bal. | bal. | bal. | bal. | bal. | bal. | bal. |

TABLE 4

Instron Percent Reduction in Combing Force

| Formula | Root | Mid-Strand | Tip | Root | Mid-Strand | Tip |
|---|---|---|---|---|---|---|
| Wet/Dry Virgin Hair (Formulations 2, 3 and 4 from Table 3) | | | | | | |
| Formula 2 (No Oats) | 21 | 24 | 29 | 15 | 17 | 21 |
| Formula 3 (Colloidal Oats) | 24 | 27 | 31 | 22 | 24 | 24 |
| Formula 4 (Processed Oats) | 79 | 81 | 82 | 65 | 66 | 68 |
| Wet/Dry Bleached Hair (Formulations 6, 7 and 9 from Table 3) | | | | | | |
| Formula 6 (No Oats) | 18 | 21 | 24 | 16 | 18 | 21 |
| Formula 7 (Colloidal Oats) | 20 | 22 | 26 | 27 | 29 | 22 |
| Formula 8 (Processed Oats) | 74 | 76 | 79 | 60 | 64 | 65 |

Transepidermal Water Loss Measurements

The measurement of transepidermal water loss ("TEWL") of the skin, after cleansing, is an industry-approved method for evaluating the mildness of cleansing formulations. Using the formulations in Tables 5, 6 and 7, Table 8 shows that TEWL is significantly reduced when oat flour is used. Table 8 also shows that the use of oat flour aids in the deposition of water-insoluble materials from cleansing-based formulations.

TABLE 5

Skin Cleaning Formulations

| Ingredient | 1 | 2 | 3 | 4 | 5 | 6 | 7 | 8 |
|---|---|---|---|---|---|---|---|---|
| Na Lauryl Sulfate | 15.0 | 15.0 | 15.0 | 15.0 | 15.0 | 15.0 | 15.0 | 15.0 |
| Lauramide DEA | 3.0 | 3.0 | 3.0 | 3.0 | 3.0 | 3.0 | 3.0 | 3.0 |
| PEG Distearate | 1.0 | 1.0 | 1.0 | 1.0 | 1.0 | 1.0 | 1.0 | 1.0 |
| Cellulosic Gum | 0.2 | 0.2 | 0.2 | 0.2 | 0.2 | 0.2 | 0.2 | 0.2 |
| Colloidal oats | — | — | 1.0 | — | — | — | 1.0 | — |
| Processed Oats | — | — | — | 1.0 | — | — | — | 1.0 |
| Oat Oil | — | 1.0 | 1.0 | 1.0 | — | 3.0 | 3.0 | 3.0 |
| Preservative | 0.1 | 0.1 | 0.1 | 0.1 | 0.1 | 0.1 | 0.1 | 0.1 |
| Fragrance | 0.5 | 0.5 | 0.5 | 0.5 | 0.5 | 0.5 | 0.5 | 0.5 |
| Water | bal. | bal. | bal. | bal. | bal. | bal. | bal. | bal. |

TABLE 6

Skin Cleaning Formulations

| Ingredient | 1 | 2 | 3 | 4 | 5 | 6 | 7 | 8 |
|---|---|---|---|---|---|---|---|---|
| Na Lauryl Sulfate | 15.0 | 15.0 | 15.0 | 15.0 | 15.0 | 15.0 | 15.0 | 15.0 |
| Lauramide DEA | 3.0 | 3.0 | 3.0 | 3.0 | 3.0 | 3.0 | 3.0 | 3.0 |
| PEG Distearate | 1.0 | 1.0 | 1.0 | 1.0 | 1.0 | 1.0 | 1.0 | 1.0 |
| Cellulosic Gum | 0.2 | 0.2 | 0.2 | 0.2 | 0.2 | 0.2 | 0.2 | 0.2 |
| Colloidal oats | — | — | 1.0 | — | — | — | 1.0 | — |
| Processed Oats | — | — | — | 1.0 | — | — | — | 1.0 |
| Petrolatum | — | 1.0 | 1.0 | 1.0 | — | 3.0 | 3.0 | 3.0 |
| Preservative | 0.1 | 0.1 | 0.1 | 0.1 | 0.1 | 0.1 | 0.1 | 0.1 |
| Fragrance | 0.5 | 0.5 | 0.5 | 0.5 | 0.5 | 0.5 | 0.5 | 0.5 |
| Water | bal. | bal. | bal. | bal. | bal. | bal. | bal. | bal. |

TABLE 7

Soap Bar Formulations

| Ingredient | 1 | 2 | 3 | 4 |
|---|---|---|---|---|
| Palm/Coconut (50/50) | 78 | 78 | 78 | 78 |
| Coconut Fatty Acid | 4 | 4 | 4 | 4 |
| Glycerin | 4 | 4 | 4 | 4 |
| Hydroxy Ethyl Cellulose | 1 | 1 | 1 | 1 |
| NaCl/Chelate Solution | 3 | 3 | 3 | 3 |
| Colloidal Oats | — | — | 1 | — |

TABLE 7-continued

Soap Bar Formulations

| | Formula | | | |
|---|---|---|---|---|
| Ingredient | 1 | 2 | 3 | 4 |
| Processed Oats | — | — | — | 1 |
| Petrolatum | — | 2 | 2 | 2 |
| Water | bal. | bal. | bal. | bal. |

TABLE 8

Transepidermal Water Loss Reduction (Percent)

| Formula | 1% Oat Oil | 3% Oat Oil | 1% Petrolatum | 3% Petrolatum |
|---|---|---|---|---|
| No Oats | No Change | <5% | No Change | <5% |
| Colloidal Oats | No Change | <5% | No Change | <5% |
| Processed Oats | 22% | 28% | 21% | 26% |

TABLE 9

Transepidermal Water Loss Reduction (Percent)

| Formula - Soap Bars | 2% Petrolatum |
|---|---|
| No Oats | No Change |
| Colloidal Oats | No Change |
| Processed Oats | 24% |

Therefore, the invention broadly provides an improved cleansing composition having at least one conditioning agent. The improved composition contains a refined agricultural grain, such as oats, that has been at least partially defatted and that has at least some of its bran removed, such that the conditioning agent will be carried by the grain to keep the conditioning agent substantially insoluble in the wetted composition.

Accordingly, while various properties and qualities of the improved formulations have been shown and described, and various modifications thereof discussed, persons skilled in this art will readily appreciate that various additional changes and modifications may be made without departing from the spirit of the invention, as defined an differentiated by the following claims.

What is claimed is:

1. In a cleansing composition having a silicone conditioning agent, the improvement which comprises:

refined oats that have been at least partially defatted and from which at least some of the bran has been removed, such that said conditioning agent will be carried by said refined oats to keep said conditioning agent substantially insoluble in the wetted composition.

* * * * *